United States Patent [19]

Löscher

[11] Patent Number: 5,952,388

[45] Date of Patent: *Sep. 14, 1999

[54] USE OF SELEGILINE FOR THE TREATMENT OF EPILEPTIC DISORDERS

[75] Inventor: Wolfgang Löscher, Hannover, Germany

[73] Assignee: Arzneimittelwerk Dresden GmbH, Radebeul, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,931

[22] PCT Filed: Jul. 27, 1995

[86] PCT No.: PCT/DE95/00981

§ 371 Date: Feb. 11, 1997

§ 102(e) Date: Feb. 11, 1997

[87] PCT Pub. No.: WO96/04897

PCT Pub. Date: Feb. 22, 1996

[30] Foreign Application Priority Data

Aug. 11, 1994 [DE] Germany ............ 442 84 446

[51] Int. Cl.⁶ .................................. A61K 31/135
[52] U.S. Cl. ............................................ 514/654
[58] Field of Search ............................... 514/654

[56] References Cited

U.S. PATENT DOCUMENTS 5,462,740  10/1995  Evenstad et al. ............ 424/436

FOREIGN PATENT DOCUMENTS 0 614 663   9/1994   European Pat. Off. .
0614663     9/1994   European Pat. Off. .
92/17169   10/1992   WIPO .

OTHER PUBLICATIONS

The Journal of Pharmacology and Experimental Therapeutics, vol. 274, No. 1, Mar. 2, 1995, pp. 307–314, Löscher, W., et al. "Anticonvulsant and Antiepileptogenic Effect . . . Epilepsy".

Indian Journal of Experimental Biology, vol. 25, No. 11, 1987, pp.761–770, Mukhopadhyay, M. et al., "Neuropharmacoligical Studies on Selective Monoamine . . . Inhibitors".

Pharamacology Biochemistry and Behaviour, vol. 23, No. 5, 1985, pp. 753–757, Sparks, D.L., et al. "Combined Inhibition Of Serotonin Uptake . . . Mice".

Mukhopadhyay et al., Indian Journal of Experimental Biology, vol. 25, pp. 761–770, 1987.

Sparks et al., Pharmacology Biochemistry & Behavior, vol. 23, pp. 753–757, 1985.

*Primary Examiner*—Raymond Henley, III
*Attorney, Agent, or Firm*—Pillsbury Madison & Sutro LLP

[57] ABSTRACT

The invention relates to the use of selegiline (=L-N-(1-phenylisopropyl)-N-methyl-N-propynylamine) or pharmaceutically utilizable salts thereof in pharmaceuticals with an antiepileptic effect.

4 Claims, No Drawings

USE OF SELEGILINE FOR THE TREATMENT OF EPILEPTIC DISORDERS

This application is a 371 of PCT/DE95/00981 filed Jul. 27, 1995.

The invention relates to the use of selegiline (=L-N-(1-phenylisopropyl)-N-methyl-N-propynylamine) or its pharmaceutically utilizable salts in pharmaceuticals with an antiepileptic effect.

It is known that selegiline is a blocker of monoamine oxidase type B. This enzyme breaks down monoaminergic neurotransmitters (especially dopamine) in gliacytes, which leads to termination of the effect of dopamine. Blockade of the enzyme results in an increase in the dopamine level in the brain. Because of this effect, selegiline is used as adjunct treatment together with levodopa in the therapy of Parkinson's disease (marketed under the proprietary name Deprenyl for example).

Further effects of N-(1-phenylisopropyl)-N-methyl-N-propynylamine and of the L form (selegiline) are described in the literature.

WO 92/17 169 A1 describes a neuroprotective effect with an as yet undefined mechanism of action. It is therefore proposed for use as neuroprotective agent (prevention of nerve cell loss in disorders of the CNS, in particular Parkinson's disease, cerebral trauma and spinal cord trauma).

Furthermore the following effects of selegiline, with or without combination partners, are patented, but no clear mechanisms of action are known for these:

Therapy of
a) immune system dysfunctions;
b) Cushing's syndrome;
c) psychological withdrawal symptoms after cocaine, alcohol and opiate addiction;
d) manifestations of ageing;
e) Alzheimer's disease;
f) psychological symptoms associated with tobacco withdrawal;
g) schizophrenia;
h) psychological symptoms associated with pre-menstrual syndrome;
i) travel sickness (kinetosis);
j) high blood pressure;
k) depression in combination with other products (U.S. Pat. No. 5,192,808, U.S. Pat. No. 4,861,800, U.S. Pat. No. 4,868,218, U.S. Pat. No. 4,579,870, CA 1 322 530, WO 92/21333 A1, WO 91/18592 A1, WO 90/04387, WO 90/01928, WO 88/04552, EP 252 290 A1)

A further use for which a patent has been applied for is as marker for glioses in degenerative disorders using labelled selegiline as marker of gliacytes (U.S. Pat. No. 7,052,921, U.S. Pat. No. 6,853,119). In this indication there is also mention of the diagnosis of gliotic centres before surgical removal of these scars from the brain of epilepsy patients. However, this is exclusively a diagnostic use. The authors state that there are no indications whatsoever of a pathogenetic involvement of monoamine oxidase B in epilepsy, selegiline is suitable only as marker for gliacytes (Kumlien E. et al., Epilepsia, Vol. 33, No. 4. 1992, 610 ff).

There are a number of anticonvulsants on the market for the treatment of epilepsies. Phenytoin and carbamezepine may be mentioned as the principal representatives. The anticonvulsants used to date for therapy lead to suppression of the convulsion but have no effect on the development of the actual epileptic focus.

It is an object of the present invention to provide pharmaceuticals with good anticonvulsant and antiepileptogenic effects.

It has been found, surprisingly, that selegiline shows a potent anticonvulsant and antiepileptogenic effect. The threshold for the induction of focal and generalized convulsions was raised to a similar extent as by the standard anticonvulsants carbamazepine and phenytoin. The convulsion threshold is regarded as the most important characteristic of an anticonvulsant effect. Epilepsy is a threshold phenomenon, and a convulsion is induced in humans by the threshold being exceeded by endogeneous or exogenous stimuli. Drugs of first choice for the treatment of epilepsy raise the threshold, while drugs of second choice often do not influence the threshold but only reduce the severity of the convulsions in the individual episode. An effect of selegiline on the threshold has also been demonstrated in a classical model of epilepsy, the maximum electric shock.

On the basis of the pharmacological investigations, selegiline shows an effect similar to that of drugs of first choice.

In epilepsy patients there is often a progression of the disorder with time, the attacks become more severe and the patient responds less well to the treatment.

It is therefore of particular interest that selegiline is also able to slow down the development of epileptic focus and thus halt progression of the disorder.

The antiepileptic effect of N-(1-phenylisopropyl)-N-methyl-N-propynylamine is strictly stereospecific. Only the L form (selegiline) has an antiepileptic effect. The D form is inactive. At doses at which the L form has no side effects, it induces severe amphetamine-like side effects.

PHARMACOLOGICAL INVESTIGATIONS

The investigation of selegiline in amygdala kindling as model of focal epilepsy and as model of epileptogenesis started from the findings on the neuroprotective effect of selegiline.

In amygdala kindling there is induction of an epileptic focus by repeated very weak stimulation of one region of the rat brain through deep electrodes. This focus is permanent, and animals which are completely kindled are to be termed epileptic. It is then possible to investigate anticonvulsants in this model. When they are given to completely kindled animals and a convulsion is induced, the threshold for induction of the convulsion may be raised (greater stimulation is necessary to induce a convulsion), and the convulsion which is nevertheless induced may be weaker.

However, it is also possible to investigate in this model drugs which—irrespective of their effect on the induced convulsion—suppress development of the epileptic focus. The anticonvulsant effect is independent of the effect on the development of the epileptic focus.

Data on the anticonvulsant effect

Method of Freeman F G et al., Brain Res. Bull 1981; 7; 629–633, modified by Rundfeldt C et al., Neuropharmacology 1990; 29; 845–851.

Amygdala kindling, raising of the threshold for induction of focal convulsions in completely kindled rats:

|  | % rise in convulsion threshold |
| --- | --- |
| L form (selegiline) | |
| 5 mg/kg i. p. | 0 |
| 10 mg/kg i. p. | +130–+250 |
| 20 mg/kg i. p. | +70 |
| 40 mg/kg i. p. | +41 |
| D form | |
| 10 mg/kg | −12 |

Effect on the development of the epileptic focus in kindling Method of Racine R et al., Electroencephalograph Clin Neurophysiol. 1975; 38; 355–365, see also Silver J M et al., Ann Neurol 1991; 29; 356–363.

When the epileptic focus is produced in the kindling there are plastic changes in the brain. Epileptic discharges with a particular total duration are necessary for complete expression of the epileptic focus. During treatment with selegiline (5 and 10 mg/kg, 1x/day) 35% and 53% more stimulations are needed until the first generalized convulsion occurs. In addition, significantly longer epileptic discharges are necessary to establish the focus (52% and 117%). This indicates that selegiline slows down the plastic changes in the brain necessary to establish the focus.

After discontinuation of the treatment, the duration of the epileptic discharges which can be induced in completely kindled animals is significantly shorter than in control animals.

This shows that the epileptic focus is less strongly expressed than in the control group.

Selegiline can thus be used as highly specific and effective medicinal substance for the treatment of epileptic disorders.

There is, moreover, not only suppression of the convulsion but also slowing down of the progression of the disorder.

The compound according to the invention and processes for its preparation are known.

The compounds can be converted in a known manner into the usual formulations such as tablets, capsules, coated tablets, pills, granules, syrups, emulsions, suspensions and solutions using inert, non-toxic, pharmaceutically suitable excipients or solvents.

In these cases the daily dose of selegiline on oral or parenteral administration should be 5–20 mg.

It is possible if necessary to deviate from the stated amounts, in particular depending on the body weight and the specific mode of administration.

What is claimed is:

1. A method for the treatment of epilepsy in a patient comprising administering to said patient an effective amount of deprenyl or salts of deprenyl to suppress the development of epileptic foci.

2. A method for slowing progression of an epileptic disorder in a patient comprising administering to said patient an effective amount of deprenyl or salts of deprenyl to slow the development of an epileptic focus.

3. A method for curing an epileptic disorder in a patient comprising administering to said patient an effective amount of deprenyl or salts of deprenyl to suppress the development of epileptic foci.

4. A method for preventing an epileptic disorder in a patient comprising administering to said patient an effective amount of deprenyl or salts of deprenyl to suppress the development of epileptic foci.

* * * * *